United States Patent
Cohen et al.

(10) Patent No.: US 10,048,193 B2
(45) Date of Patent: Aug. 14, 2018

(54) CONVEX LENS-INDUCED CONFINEMENT FOR MEASURING DISTRIBUTIONS OF MOLECULAR SIZE

(71) Applicant: President and Fellows of Harvard College, Cambridge, MA (US)

(72) Inventors: Adam E. Cohen, Cambridge, MA (US); Sabrina R. Leslie, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/234,964

(22) Filed: Aug. 11, 2016

(65) Prior Publication Data

US 2017/0160188 A1    Jun. 8, 2017

Related U.S. Application Data

(63) Continuation of application No. 13/521,425, filed as application No. PCT/US2011/021403 on Jan. 14, 2011, now abandoned.

(Continued)

(51) Int. Cl.
*G01N 15/14* (2006.01)
*G02B 21/16* (2006.01)
(Continued)

(52) U.S. Cl.
CPC ......... *G01N 15/1436* (2013.01); *G02B 21/16* (2013.01); *G02B 21/34* (2013.01);
(Continued)

(58) Field of Classification Search
CPC .... G01N 15/00; G01N 15/02; G01N 15/0205; G01N 15/0227; G01N 15/10;
(Continued)

(56) References Cited

U.S. PATENT DOCUMENTS 5,037,202 A   8/1991  Batchelder et al.
6,180,314 B1 * 1/2001  Berndt ............... G01N 1/2813
                                                        422/401

FOREIGN PATENT DOCUMENTS

EP    0479231 A1    4/1992
EP    0961110 A2   12/1999
(Continued)

OTHER PUBLICATIONS

Enomoto et al., "Simple and Precise Size-Separation of Microparticles by a Nano-Gap Method", Analytical Sciences, May 2009, vol. 25, pp. 605-610.*

(Continued)

*Primary Examiner* — Stephone B Allen
*Assistant Examiner* — Adam W Booher
(74) *Attorney, Agent, or Firm* — Wilmer Cutler Pickering Hale and Dorr LLP

(57) ABSTRACT

A curved surface is placed tangent to a slide and displaces a sample liquid from the point or line of contact outward. Imaging indicates a region where fluorescence is observed, and the location of the fluorescence indicates the molecular size. The radius of curvature of the lens is known, the distance from the (center) point of contact of the observed fluorescence is measured with a microscope and the distance of the lens surface to the slide's surface can then be calculated. This distance represents the size of the molecule or ensemble of molecules emitting. Similarly, absorbance, etc. could be measured with a light source below the slide.

14 Claims, 12 Drawing Sheets

Related U.S. Application Data

(60) Provisional application No. 61/295,492, filed on Jan. 15, 2010, provisional application No. 61/378,160, filed on Aug. 30, 2010.

(51) Int. Cl.
*G02B 21/34* (2006.01)
*G06T 7/00* (2017.01)

(52) U.S. Cl.
CPC ...... *G06T 7/0012* (2013.01); *G01N 2015/144* (2013.01); *G01N 2015/1493* (2013.01); *G06T 2207/10056* (2013.01); *G06T 2207/10064* (2013.01)

(58) Field of Classification Search
CPC .............. G01N 15/14; G01N 15/1404; G01N 15/1425; G01N 15/1434; G01N 15/1436; G01N 2015/0038; G01N 2015/0053; G01N 2015/0065–2015/0088; G01N 1/28; G01N 2001/282; G01N 2001/366; G01N 21/00; G01N 21/03; G01N 21/64; G01N 21/6456; G01N 21/6428; G01N 21/6447; G01N 21/6458; G01N 2021/036; G01N 2021/0364; G01N 33/48; G01N 33/49; G02B 21/00; G02B 21/0076; G02B 21/16; G02B 21/32; G02B 21/33; G02B 21/34; G02B 21/36; G02B 21/361; G02B 21/365; G06T 7/0012; G06T 2207/10056; G06T 2207/10064
See application file for complete search history.

(56) References Cited

FOREIGN PATENT DOCUMENTS

| | | |
|---|---|---|
| EP | 1219963 A1 | 7/2002 |
| WO | WO-99/44593 A1 | 9/1999 |

OTHER PUBLICATIONS

Monjushiro et al., "Size sorting of biological micro-particles by Newton-ring nano-gap device", Journay of Chromatography A, 1106, 2006, pp. 205-210, available online Dec. 7, 2005.*

Hatta et al., "Micro-particle Sorting by Newton-ring Device," Chem. Commun., Oct. 11, 2004, pp. 2772-2773.

International Search Report and Written Opinion of the International Searching Authority, the European Patent Office, for International Application No. PCT/US2011/021403, dated May 16, 2011, 11 pages.

Peterson et al., "Three-dimensional Particle Tracking Using Micro-Particle Image Velocimetry Hardware," Measurement Science and Technology, Oct. 6, 2008, 19, 8 pages.

Shaner et al., "A Guide to Choosing Fluorescent Proteins," Nature Methods, vol. 2, No. 12, Dec. 2005, pp. 905-909.

* cited by examiner

CONVEX LENS-INDUCED CONFINEMENT FOR MEASURING DISTRIBUTIONS OF MOLECULAR SIZE

RELATED APPLICATIONS

This application claims priority to co-pending U.S. Provisional Application No. 61/295,492, filed Jan. 15, 2010, and U.S. Provisional Application No. 61/378,160, filed Aug. 30, 2010. The contents of those applications are incorporated by reference.

STATEMENT OF GOVERNMENT RIGHTS

This invention was made with government support under CHE-0910824 awarded by the National Science Foundation. The government has certain rights in the invention.

INCORPORATION BY REFERENCE

All patents, patent applications and publications cited herein are hereby incorporated by reference in their entirety in order to more fully describe the state of the art as known to those skilled therein as of the date of the invention described herein.

BACKGROUND

The subject matter is directed to systems and methods for determining the size of a molecule, or, more generally, the distribution of sizes of an ensemble of molecules.

Gel electrophoresis is the most commonly used technique for measuring distributions of molecular sizes. In its usual application to proteins, the proteins are denatured so the electrophoretic mobility measures the molecular length, and thereby the approximate molecular weight. Native gel electrophoresis can also be applied to biomolecules in their functional conformation, though the interpretation of mobilities in native gels is often ambiguous. Gel electrophoresis cannot be applied to large or weakly associating molecular complexes. Additionally, gel electrophoresis typically requires several hours to run, requires large amounts of sample, and consumes ~100 mL of reagents.

The sizes of particles larger than ~10 nm diameter can be determined by dynamic light scattering (DLS). All particles scatter light, so dust or impurities confound or interfere with DLS measurements, and DLS can only be applied to the major component in a heterogeneous mixture. Furthermore, the inverse Laplace transform used in interpretation of DLS is subject to noise, so DLS measurements are often imprecise.

Fluorescence correlation spectroscopy (FCS) measures the size of fluorescent species in solution by measuring the distribution of residence times in a focused laser spot. FCS works best for small molecules, with hydrodynamic radii of less than 20 nm. As with DLS, FCS cannot easily distinguish between individual particles and fluorescent aggregates. FCS provides only a very coarse measure of molecular size, and is not well suited to measuring heterogeneous size distributions.

SUMMARY

A simple system that measures the size and/or size distributions of imageable molecules in solution is provided. The present system and method provide means to determine the size of a molecule, or more generally, the size distribution of a population of molecules.

In one aspect, a system for detecting the size of a molecule is provided. The system includes a sample measurement surface having a curved cover plate positioned tangent to a planar surface, e.g., there is a single point or line of contact, and the curved cover plate has a surface that varies in a predetermined and understood manner from the point of contact to a radially displaced position relative to the point of contact. The system also includes an imaging system such as an inverted fluorescent microscope. The system is capable of detecting molecules in solution, with molecular diameters in the size range of ~2-1000 nm. The imaging system is capable of detecting molecules, e.g., either by absorption, by fluorescence or other technique. The transparent material can be wedged shaped or curvilinear. By way of example, it can be a convex, biconvex, plano-convex lens, or concave convex lens where the curvature of the surface is well-defined.

In one aspect, a method for detecting the size of a molecule is provided. The method includes applying a test liquid containing molecules to be measured to the sample measurement surface. Measuring the location of the fluorescence from the point of contact, wherein the location of fluorescence is an indication of the molecular size. Similarly, other properties of the sample, absorbance, etc. could be measured with a light source below the sample measurement surface to determine onset of molecular exclusion.

The radius of curvature of the transparent material is known. The distance from the (center) point of contact to the observed fluorescence is measured and the distance (or spacing) of the curved surface to the planar surface can then be calculated. This distance correlates with the size of the molecule or collection of molecules. The phenomenon of excluding particles from regions under the curved surface that are smaller than the molecular diameter is referred to as "nanoscale confinement."

The system for detecting the size of a molecule can operate with low analyte amounts, e.g., ~10 µL of a ~1 nM solution of analyte, acquires the data in ~1 minute, works in the presence of a high concentration of non-fluorescent background, and is simple to construct and operate.

The methodology can be used to determine the sizes of freely diffusing molecules with diameters ranging from 2 nm to 1000 nm by imaging their areal density as a function of the nanoscale confinement. For example, the method and device can be used to detect the molecular size of biomolecules such as proteins, micelles and DNA. It can also be used to detect the molecular size of polymers, in particular polymer beads. The methodology is suited to measuring the size of a homogeneous sample population as well as the size distribution of a heterogeneous sample population.

A simple method for imaging single molecules in free solution is disclosed. The system confines molecules in a nanoscale wedge-shaped gap formed between a curved surface and a planar surface. The sub-wavelength confinement leads to up to 20-fold greater rejection of background fluorescence than is achieved with total internal reflection fluorescence (TIRF) imaging, and approximately 10,000-fold longer per-molecule observation time than is achieved with confocal detection. The system provides information relating to the nanoscale optical and mechanical properties of single molecules, without relying on nanofabrication or nanopositioning equipment.

The system for detecting size of a molecule includes a sample measurement surface having a convex surface positioned tangent to a planar surface, coupled with an imaging system such an inverted fluorescent microscope. In one or more embodiments, the convex surface comprises a lens and the system is referred to as a convex lens-induced confinement system (CLIC). In one or more embodiments, the system comprises a flow cell having two substantially planar surfaces, one of which can be deflected to form a convex surface, and the system is referred to as a flow cell-convex lens-induced confinement system (FC-CLIC).

In one aspect, a method for detecting size of a molecule, includes applying a liquid sample containing molecules to be measured to a sample measurement surface; contacting the sample measurement surface with a curved surface positioned tangent to the sample measurement surface at a point or line of contact, said curved surface having a surface that varies in a predetermined and understood manner from the point or line of contact to a displaced position relative to the point or line of contact; subjecting the sample to imaging to identify a region where sample is present; and determining the location of the sample presence from the point of contact outward, wherein the location of the sample is an indication of molecular size.

In one or more embodiments, the imaging detects fluorescence, or the imaging detects light absorbance.

In any of the preceding embodiments, the curved surface includes a convex lens, and for example, the convex surface is selected from the group consisting of convex, biconvex, plano-convex, and concave convex lenses, or the curved surface comprises a cylindrical lens.

In any of the preceding embodiments, the curved surface is obtained by deflecting a flexible sheet disposed above the sample measurement surface into contact with the sample measurement surface.

In any of the preceding embodiments, the method further includes correlating the location of the fluorescence with a distance of the lens surface to the planar surface, said distance representing a molecular dimension of the molecules.

In any of the preceding embodiments, molecule size is determined, or molecule size distribution is determined, or molecular aspect ratio is determined.

In any of the preceding embodiments, fluorescent imaging provides a gradual transition from a dark region to a bright fluorescence region.

In any of the preceding embodiments, molecular aspect ratio is determined.

In any of the preceding embodiments, the molecular size ranges from about 2 nm to about 1000 nm.

In any of the preceding embodiments, the sample measurement surface comprises a flow cell having an upper and a lower surface for receiving a sample to measured, and the convex surface is provided by deflecting the upper surface of the flow cell downward to the lower surface of the flow cell to create the contact point.

In any of the preceding embodiments, the method further includes coating the convex surface and/or the sample measurement surface with a non-stick coating.

In any of the preceding embodiments, the molecule is a biomolecule, for example, proteins, micelles or DNA, or a polymer molecule, for example, polymer beads.

In any of the preceding embodiments, the sample measurement surface and/or the curved surface comprises surface features, and for example, the surface features are selected from the group of dimples and posts.

In another aspect, a system for detecting size of a molecule, includes a sample measurement zone having a convex surface positioned tangent to a planar surface, coupled with an inverted fluorescent microscope positioned to detect the presence of a molecule of interest in the sample measurement zone.

In another aspect, a system for detecting size of a molecule, includes a sample measurement zone having a convex surface positioned tangent to a planar surface, coupled with an imaging device capable of detecting the presence of a molecule of interest present in the sample measurement zone.

In any of the preceding embodiments, the imaging device is capable of detecting light absorbance or fluorescence.

In any of the preceding embodiments, the molecule of interest is a biomolecule, for example, proteins, micelles or DNA, or a polymer molecule, for example, polymer beads.

In any of the preceding embodiments, comprising a translation stage for positioning the convex surface in the x-, y-, and z-directions.

In any of the preceding embodiments, the convex surface comprises a convex lens, and for example, the convex surface is selected from the group consisting of convex, biconvex, plano-convex, and concave convex lenses.

In any of the preceding embodiments, the lens is coupled with a counterweight to reduce the resting force of the lens on the planar surface.

In any of the preceding embodiments, the convex surface is coated with an anti-stick coating.

In any of the preceding embodiments, the sample measurement zone comprises a flow cell for receiving a sample to measured, said flow cell comprising upper and lower sheet spaced apart from one another a distance defined by side walls.

In any of the preceding embodiments, the system further includes a deflector, positioned above the flow cell, for reversibly deflecting the upper surface of the flow cell into contact with the lower surface of the flow cell to form the convex surface of the sample measurement zone.

In any of the preceding embodiments, the system further includes a translation stage for positioning the convex surface in and out of deformation contact with the flow cell.

In any of the preceding embodiments, the width of the flow cell varies along its length.

In any of the preceding embodiments, the system further includes imaging software or particle tracking software.

In another aspect, a method for detecting size of a molecule, includes applying a liquid sample containing molecules to be measured to a sample measurement zone, the sample measurement zone having a transparent material positioned tangent to a planar surface, said material having a surface that varies in a predetermined manner from the point of contact to a radially displaced position relative to the point of contact; subjecting the sample to fluorescent imaging to identify a region where the fluorescence is observed; and determining the location of the fluorescence relative to the point of contact, wherein the location of the fluorescence is an indication of molecular size.

In any of the preceding embodiments, the transparent material is wedge-shaped.

In any of the preceding embodiments, the transparent material is curvilinear.

BRIEF DESCRIPTION OF THE DRAWINGS

Various objects, features, and advantages of the present invention can be more fully appreciated with reference to the following detailed description of the invention when considered in connection with the following drawings, in which like reference numerals identify like elements. The following drawings are for the purpose of illustration only and are not intended to be limiting of the invention, the scope of which is set forth in the claims that follow.

DETAILED DESCRIPTION

Figure 1:
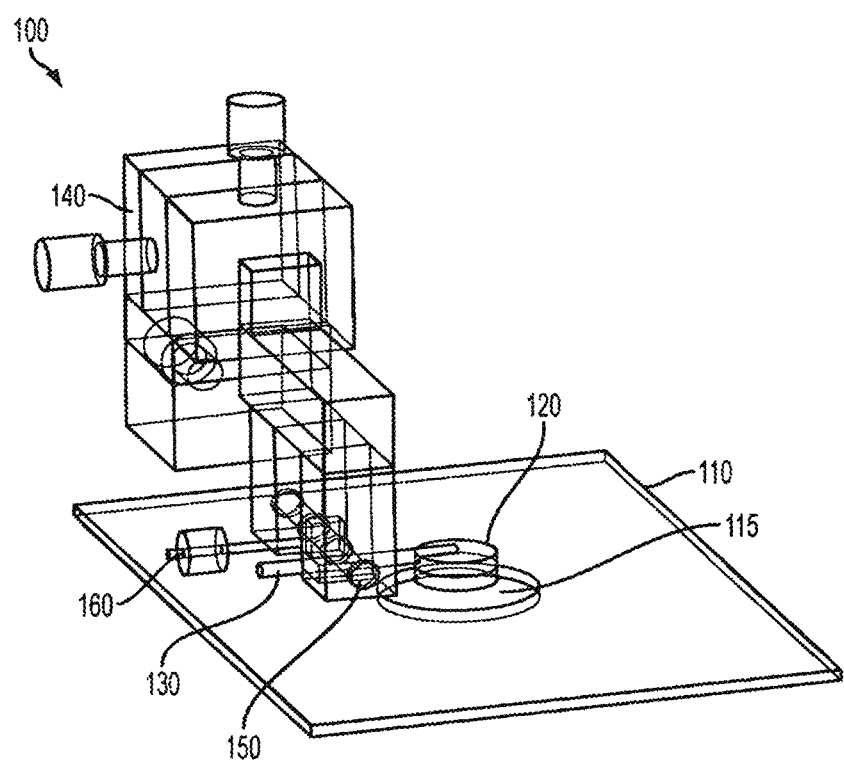
FIG. 1 is a schematic illustration of a convex-lens induced confinement system according to one or more embodiments.

The Convex (or Cylindrical) Lens-Induced Confinement (CLIC) or the flow cell Convex (or Cylindrical) Lens-Induced Confinement system (FC-CLIC) system determines the distribution of molecular sizes by measuring the density profile of molecules confined in a wedge-shaped gap. Molecules are excluded from regions where the height of the gap is less than the diameter of the molecule. Under imaging conditions, a dark region is observed where molecules are excluded due to their size. A fluorescent image centered on the point of contact shows a disk inside of which there is no fluorescence. A bright area is observed outside the disk where molecules are located. Although this method is described using fluorescence as the imaging mode, other imaging or detection techniques can be implemented within the scope of the method. For example, the method can be used with any optical microscopy technique that can be performed in an inverted microscope. Exemplary fluorescence microscopy imaging techniques include epifluorescence, total internal reflection fluorescence (TIRF), confocal, and two-photon microscopy, for example. In addition, the method can be used with differential interference contrast (DIC), dark-field, Raman, and coherent anti-Stokes Raman (CARS) microscopy.

The CLIC or FC-CLIC device provides a direct measure of the diameter of imageable molecules in solution, offering a dynamic range of 2 nm to 3 µm, or 2 nm to 1000 nm, and handling freely diffusing molecules in their native form. Measurements require only 10 µL of solution at an analyte concentration of only 1 nM, and may be performed in less than one minute.

The CLIC or FC-CLIC device employs wedged shaped or curvilinear surface to generate a surface that varies in its distance in a known manner from a planar surface on which it is disposed. In one or more embodiments, the curvilinear surface can be a convex, biconvex, plano-convex lens, or concave convex lens where the curvature of the surface is well-defined. When the lens is placed in contact with a planar surface, it forms a point contact. In other embodiments, the curvilinear surface can be a cylindrical lens. A cylindrical lens is a lens which focuses light which passes through on to a line instead of on to a point, as a spherical lens would. The curved face or faces of a cylindrical lens are sections of a cylinder. When the lens is placed in contact with a planar surface, it forms a line contact.

In one embodiment, the CLIC system includes a plano-convex lens, curved side down, resting on top of a coverslip or other flat, transparent surface. See, e.g., FIG. 3A. Due to the curved nature of the lens surface, it contacts the flat surface at a single point. The region near the point of contact between the lens and the coverslip is imaged using an inverted fluorescence microscope. The lens-coverslip distance varies smoothly from zero at the point of contact, to hundreds of microns at radii far from the point of contact, according to the equation:

$$h \approx \frac{1}{2}\frac{r^2}{R},$$

where r is the distance from the point of contact and R is the radius of curvature of the lens. Near the point of contact, a displacement of tens of microns in the x-y plane leads to a nanometer-scale change in the thickness of the gap. In a typical field of view of 100 µm, with a 100 mm focal length lens (R=4.6 cm), the gap varies from 0 to 27 nanometers. From the radius of the excluded region, r, and the known radius of curvature of the lens, R, one can extract the diameter of the molecules, h. This measurement has an accuracy of ~2 nm. Locations and measurements of imaged particles can be accomplished using conventional methods. By way of example, three-dimensional particle tracking is described by Peterson et al., in Meas. Sci. Technol. 19 (2008) 115406, which is incorporated in its entirety by reference. Similar relationships are found for the convex surface generated in FC-CLIC, where the convex surface is generated using deflection of a flexible planar surface.

The accuracy of the confinement is determined, in part, by how well the curvature of the lens is known. This curvature can be measured to high accuracy in situ using optical interferometry. The precision of the confinement is a function of the surface roughness of the lens and the coverslip. The surfaces should be relatively smooth. Fused silica optics are commercially available with root mean square (RMS) surface roughness <1 nm. To accurately detect the confinement of molecules in the resulting gap, the sheets should be flat on the length scales of the molecules of interest. Typically, the sheets have a RMS surface roughness less than about 1 nm. Acceptable ranges of surface roughness depend on the size of the molecules to be measured: for a molecule of diameter x, the surface roughness should be less than x/3 or more preferably less than x/5 or most preferably less than x/10. In some embodiments, the surface can be patterned, for example by lithography. Surface features can provide a further level of molecular confinement. For example, a surface can include an array of posts or dimples (see FIGS. 9C to 9E). The posts constrain the molecules between posts in addition to the constraint based upon the radius of curvature of the convex surface.

Figure 3A:
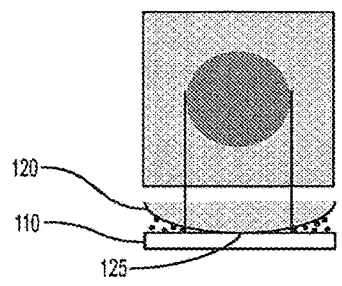
FIGS. 3A and 3B are a schematic illustration demonstrating the determination of molecular size for FIG. 3A, a low aspect molecule and FIG. 3B, a high aspect molecule.

In a substantially monodisperse population, molecules will distribute uniformly throughout the liquid sample due to Brownian motion. However, the molecules will be physically excluded from areas under the lens where the gap is less than the molecule dimension. For a uniformly sized population of molecules, there is a fairly abrupt cutoff of fluorescence. See, FIG. 3A. The system determines the distribution of molecular sizes directly by measuring the density profile of molecules confined in a wedge-shaped gap. Simply, molecules are excluded from regions in which the gap height is less than the molecular diameter. In considering an idealized sample of hard spheres, a fluorescent image centered on the point of contact shows a disk inside of which there is no fluorescence (FIG. 3A). In a heterogeneous population of real molecules, the cutoff is gradual, and the shape of the cutoff indicates the distribution of molecular sizes.

Figure 3B:
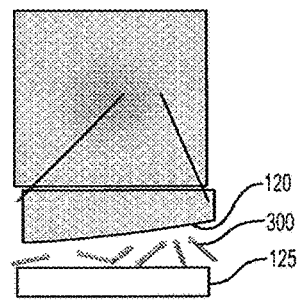

The CLIC and FC-CLIC systems also allow one to learn about the aspect ratio of anisotropic particles. For rodlike particles, for instance, there is an entropic penalty to enter the region where there is orientational confinement, but the particles are not completely excluded until the confinement is less than the diameter of the rod. FIG. 3B illustrates the various orientations of an aspected particle 300 in the area under the lens a distance away from the central point of contact. By measuring the profile of particle density as a function of confinement, one can extract information about the length and aspect ratio of an asymmetric object. Such a technique is well suited to determine the size and shape of virus particles or amyloid fibrils, for example.

In a heterogeneous population of molecules, molecules of different sizes occupy different locations in the gap. Since molecules are excluded from regions in which the gap height is less than the molecular diameter, larger molecules are excluded at a greater distance from the contact point, Since molecules are expected to randomly distribute throughout the area where the gap height is greater than molecule dimension, the resulting cutoff of fluorescence is gradual, and the shape of the cutoff indicates the distribution of molecular sizes.

The distribution of molecules and their size can be extracted from the pattern of fluorescence intensity using available imaging software. Fluorescence images are loaded into analysis software, bright regions are identified as fluorescent molecules and their spatial density profile is determined. In addition, particle tracking software can be employed to characterize their diffusion.

Figure 2:
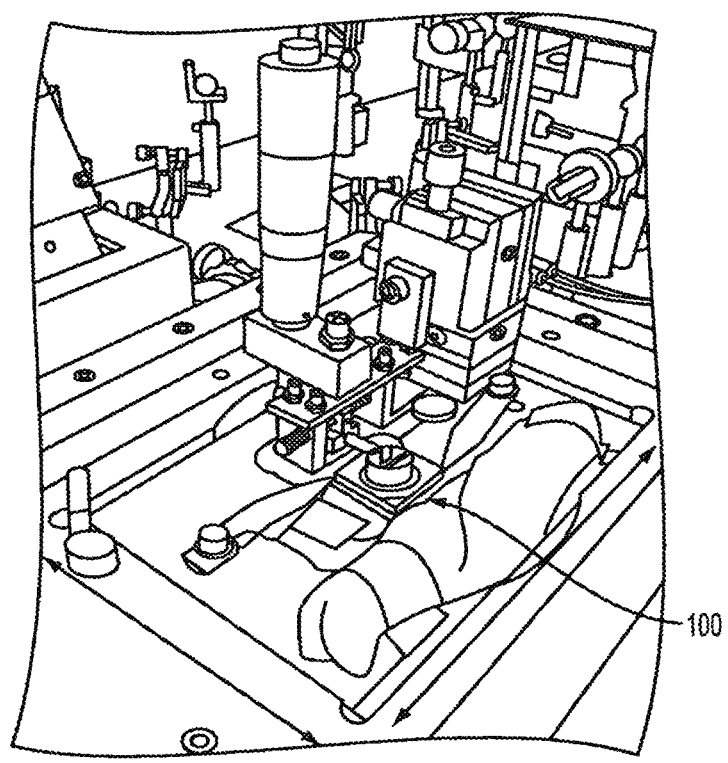
FIG. 2 is a schematic illustration of a convex-lens induced confinement system according to one or more embodiments.

An apparatus according to one or more embodiments for the determination of molecular size using convex lens induced confinement is shown in FIG. 1. The apparatus is of a size that permits it to be integrated with conventional imaging instruments such as an inverted fluorescent microscope. FIG. 2 shows a schematic illustration of an exemplary convex lens induced confinement apparatus 100 resting atop a microscope stage. In this particular embodiment, the apparatus is about 4"×5" in area, although it may take on any size and can be even smaller.

One embodiment of the apparatus is described with reference to FIGS. 1, 3A and 3B. The system employs an imaging microscope, e.g., a fluorescence microscope, including a high numerical aperture objective and an electron-multiplying CCD camera. The convex lens induced confinement apparatus 100 rests atop the microscope stage and includes a planar surface 110 having a sample measurement surface 115. The surface can include a glass coverslip (not shown) that can be disposed of or replaced after use. The surface is typically transparent to permit imaging of the sample from a light source below the microscope stage. The light source can be a laser, lamp or light emitting diode (LED). The convex lens induced confinement apparatus also includes a convex lens 120 that is positioned with its curved surface facing the planar surface 110. In some embodiments, the surface of the lens and/or the coverslip can be coated with a non-stick surface coating to reduce adhesion of molecules to the surfaces. When the lens 120 is lowered into contact with the planar surface, it contacts at a single point 125 (shown on FIGS. 3A and 3B). The lens can include a handle 130, typically attached to the back (planar) side of the lens, to aid in the positioning of the lens. The positioning handle is attached to an xyz translation stage 140 that provides for positioning capability in x-, y- and z-directions. Handle 130 is mounted to the translation state at pivot 150 that moves the lens in the z-direction. Counterweight 160 can be used to balance the weight of the lens so that the lens rests lightly on the surface of the sample measurement surface and does not distort the surface.

Figure 9A:
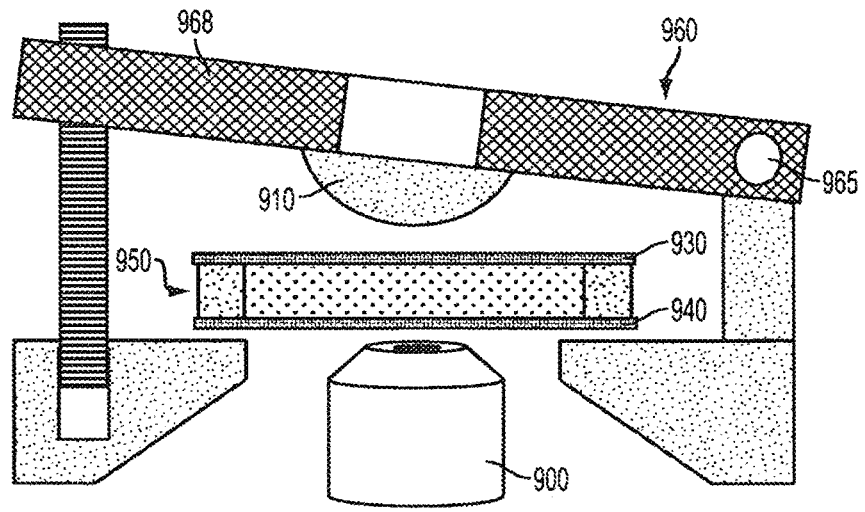
FIGS. 9A and 9B are schematic illustrations of a flow cell CLIC system according to one or more embodiments in which the convex lens is in a (FIG. 9A) raised or (FIG. 9B) lowered position.
Figure 9B:
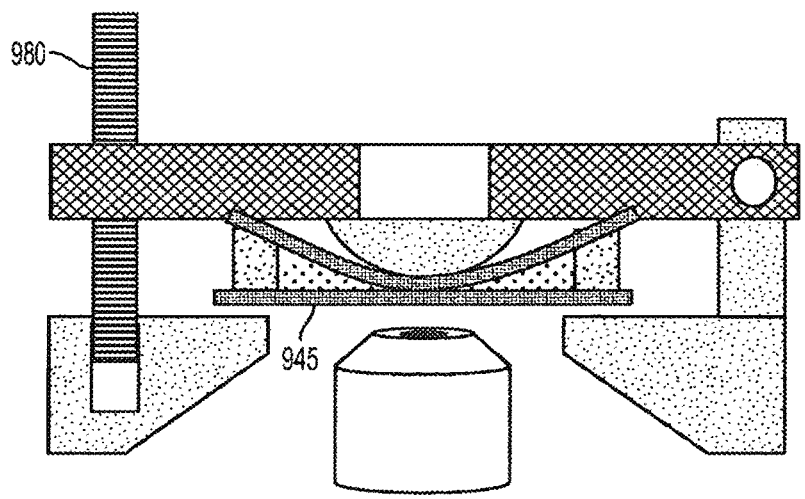

Another version of the CLIC apparatus is illustrated in FIGS. 9A and 9B, which is referred to as Flow Cell CLIC (FC-CLIC). As in the system shown in FIG. 1, the Flow Cell CLIC apparatus includes an imaging microscope 900 with similar features. The Flow Cell CLIC system also includes a convex lens 910 that can be raised and lowered into contact with the top surface of the flow cell 950. As with CLIC, Flow Cell CLIC (FC-CLIC) confines molecules to a nanoscale gap. In CLIC, the gap is formed between the surfaces of a lens 120 and coverslip 125 (See, e.g., FIG. 3A). In FC-CLIC, the sample is inserted between two initially planar sheets of transparent material 930, 940, e.g., glass or fused silica, which make up the top and bottom surfaces of a flow cell, respectively. The top surface should be flexible, e.g. by using a thin glass sheet. The lens or other rounded object 910 presses down upon the top sheet 930 of the flow cell, causing it to bow downward until it makes contact with the bottom sheet 940 at a single point 945. See, FIG. 9B. Molecules are imaged in the annular wedge-shaped gap surrounding the point of contact, as is described above. The convex surface can be raised or lowered onto the flow cell from a support 960. Support 960 includes a lever 968 that can be pivotable, e.g. from hinge 965, to lower and raise the convex surface 910, which is attached to a lower surface of lever 968. The hinge permits the lens surface to be moved out of the way for ease of access to the sample.

Adjustments to the lens position can be made on a fine-pitch screw 980 that is integrated into the aluminum lever and which conveys the motion to a small convex lens 910, which pushes down on the top coverslip. This arrangement provides highly precise and reproducible formation of a nanoscale gap. By using a transparent lens to apply pressure to the top coverslip, optical access to both sides of the flow cell is maintained. This access is useful for illuminating the sample from both sides. The lens is optionally made of an elastomeric material such as poly(dimethyl siloxane), so that it does not scratch the flow cell at the point of contact.

The present design could be augmented by addition of a motorized positioner to apply pressure to the top coverslip. The positioner can have x, y, z-axis mobility for precise location of the convex surface. The positioner can be manually controlled or automated.

Figure 9C:
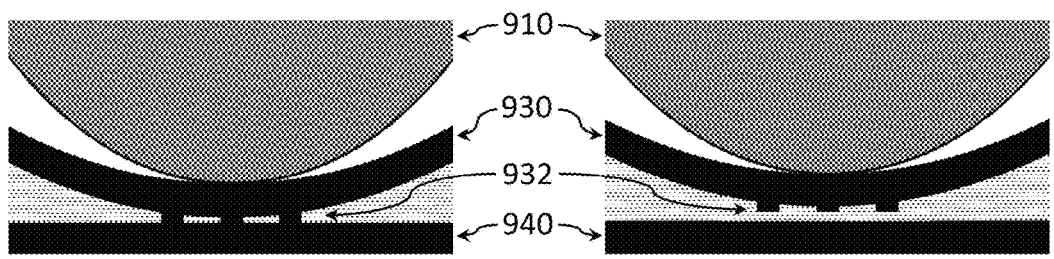
FIGS. 9C, 9D and 9E are schematic illustrations showing posts (FIG. 9C), dimples (FIG. 9D) and a combination of posts and dimples (FIG. 9E) that can be present on inner surface(s) of a flow cell, when the convex lens is in a lowered position (left side) or in a raised position (right side).
Figure 9D:
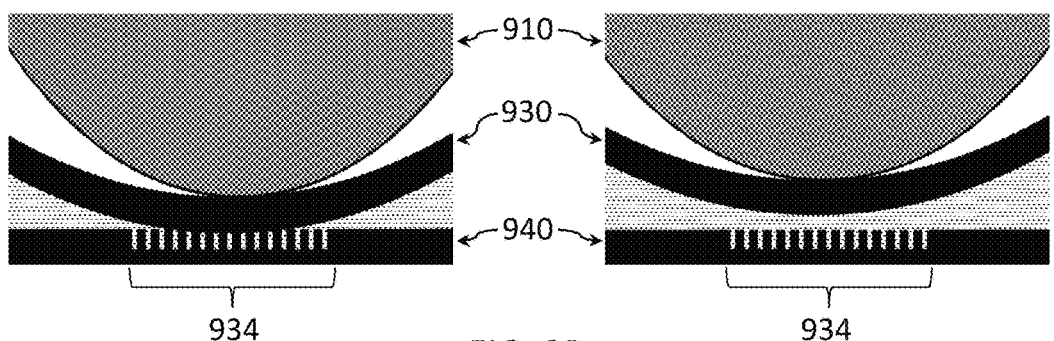
Figure 9E:
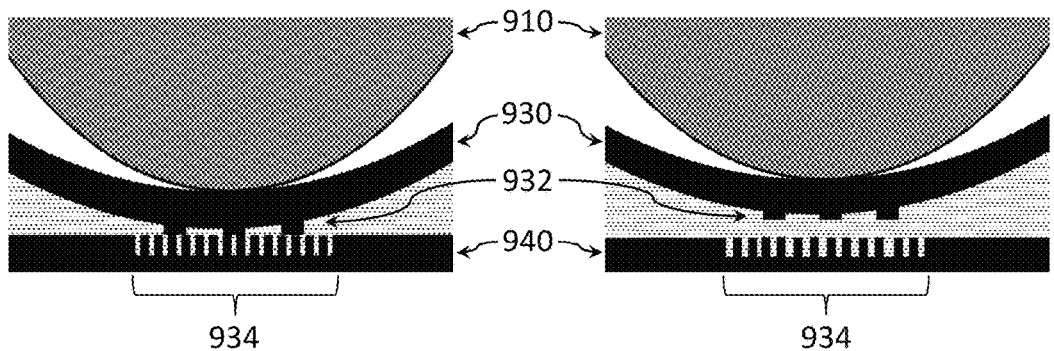
Figure 10:
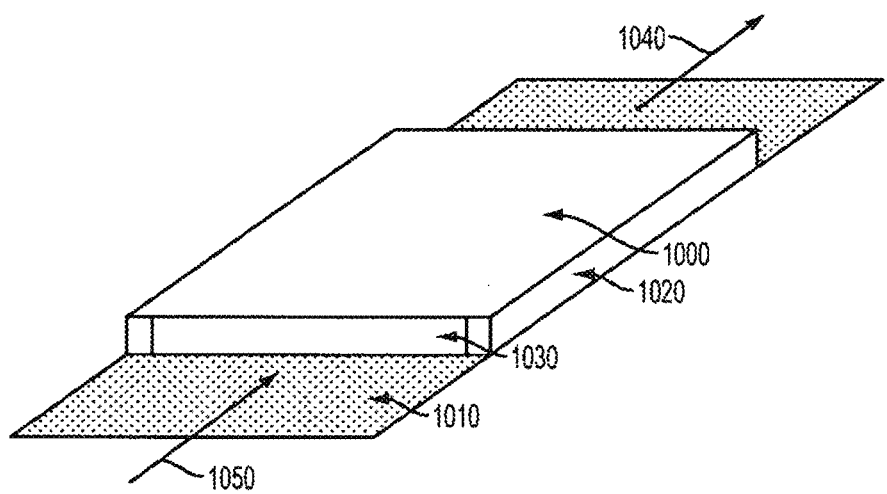
FIG. 10 is a schematic illustration of a flow cell according to one or more embodiments.

An exemplary flow cell is illustrated in FIG. 10. The flow cell is made up of two sheets of material 1000 and 1010, which serve as the top and bottom surfaces of the flow cell, respectively. The sheets are transparent, e.g., transparent to the light used to analyze the sample, and the top surface is flexible, e.g., capable of bending or being displaced from the resting position indicated in FIG. 9A and the displaced position indicated in FIG. 9B. The sheets can be made from glass or fused silica. In some instances the sheets can be made of plastics, so long as they have the required transparency. For fluorescence measurements, it is desirable for the sheet material to have low autofluorescence. In addition, the sheets should be relatively smooth. In order to accurately detect the confinement of molecules in the resulting gap, the sheets should be flat on the length scales of the molecules of interest. Ideally, the sheets have a RMS surface roughness <1 nm, although for applications with larger molecules RMS surface roughness as large as 10nm is acceptable. In some embodiments, the surface can be patterned, for example by lithography. Surface features can provide a further level of molecular confinement. For example, as illustrated in FIGS. 9C to 9E, a surface can include an array of posts 932 or dimples 934. The posts constrain the molecules between posts in addition to the constraint based upon the radius of curvature of the convex surface.

The flow cell includes side walls 1020 that define a spacing or gap 1030 between the upper and lower sheets 1000, 1010. The initial gap can range from a few microns, e.g., about 5 μm to about 500 μm. The amount of fluid needed for the space is therefore small and typically is about 10 μL. The side walls can be made of any suitable spacer or adhesive that provides the desired gap dimensions. By way of example, the side walls can double sided tape, polymer or plastic stripes, or glue or other adhesive, e.g., an epoxy adhesive. The flow cell is significantly larger than the test area, and has typical dimensions of 100 μm (vertical) by 7-12 mm (horizontal) (but can be smaller or larger than this). Because the test surface (typically on the order of 150 μm) is so much smaller than the overall flow cell and surface substantially centrally located, its distance from the side walls and the material selection for the side walls is not critical. The side walls are shown only on the long lengths of the flow cell; however, the flow cell can include front and rear walls of the flow cell as well.

Liquid is introduced into the flow cell at a suitable aperture. The apertures can include slots 1040, 1050 at the front and rear sides of the flow cell, as illustrated in FIG. 10. The slots can make up a full length of the flow cell or a portion thereof. In other embodiments, the apertures may be provided along the length of the side walls. In one or more embodiments, the side walls, front and rear walls are sealed, and apertures are provided in the upper and/or lower sheets of the flow cell.

Figure 11:
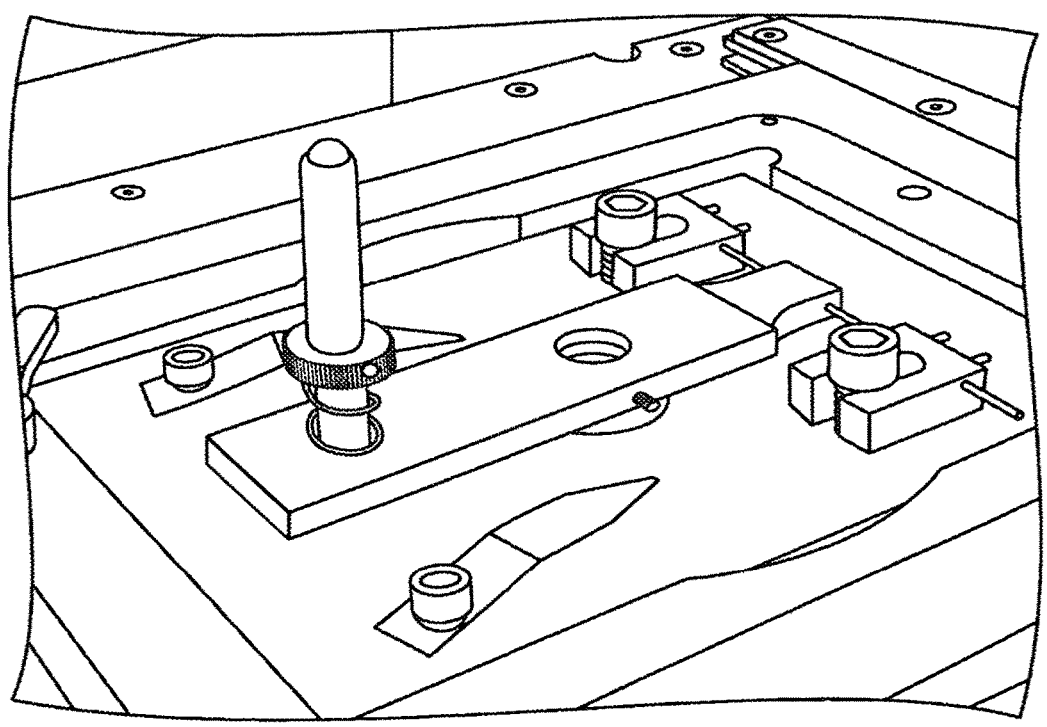
FIG. 11 is a photograph of an exemplary flow cell CLIC system.

In one exemplary embodiment, the flow cell channel is constructed using two parallel strips of double-sticky tape, sandwiched between two coverslips. Fluid flows through the gap between the pieces of tape, which has typical dimensions of 100 μm (vertical) by 7-12 mm (horizontal) by 25 mm (length). The width, height and length of the channel determine the volume of the cell, as well as the radius of curvature of the top coverslip at the point of contact. Furthermore, the lateral edges of the flow cell could be constructed of a more durable material than double-sided tape. An exemplary FC-CLIC is shown in FIG. 11.

In instances where a flowable adhesive is used, a consistent spacing of the desired gap dimension can be obtained by inserting a plastic sheet of the desired gap dimension between the upper and lower sheets of the flow cell. The plastic insert is smaller than the flow cell sheets so that the flow cell sheets extend beyond it on both lengths to define an open channel. The adhesive is applied in the channel and allowed to dry or at least to obtain sufficient mechanical strength to maintain the spacing between the two sheets, at which point the plastic insert can be removed.

The curvature of the flow cell during use is determined by various factors, such as the gap dimension and the width of the flow cell channel. For example, a vertical large gap will result in a steeper curvature (e.g. smaller radius of curvature), all other things equal. Similarly, increasing the width of the flow cell channel will reduce curvature (e.g., increase the radius of curvature). The point of contact can be varied to avoid locations in the flow cell where the glass surface has become contaminated, for example, by the sticking of test molecules to the glass surface. If the width of the flow cell channel varies along the length of the flow cell, e.g., by arranging that its walls are not parallel to one another but instead oriented at an angle, then by translating the lens along the length of the flow cell, one can vary the radius of curvature of the gap geometry. The actual geometry of the surface can be calculated, either prior to testing or in real time (in situ).

FC-CLIC offers several advantageous features. FC-CLIC is simple to set up and operate. The flow cell at the heart of the device is widely used in many biology labs, so the design will be familiar to prospective users.

The volume of the sample is small and can be 10-fold smaller sample volume than in CLIC (ca, 10 μL for FC-CLIC vs. ca. 100 μL for CLIC). The small sample volume is possible due to reduced evaporative losses because the flow cell is a mostly closed system. As the liquids evaporate and the solution concentrates, properties and characteristics of the molecules can change. In CLIC, the sample size is selected to be sufficiently large that evaporative losses are minimal. In FC-CLIC, there is no such constraint. In addition, the closed cell set up of the flow cell reduces exposure of the sample to ambient gases, particularly oxygen.

Simple chemical functionalization of top and bottom confining surfaces is readily available. It may be desirable to functionalize the sample holder surface to enhance or inhibit sample binding to the sample holder or the convex surface. In other embodiments, it may be desirable to monitor the interaction between the molecules of interest in solution and functionalized molecules on the sample holder surface. While it is possible to functionalize either the lower coverslip surface or the convex surface used in CLIC systems, the functionalization of the glass or fused silica used as coverslips is well known and easy.

The samples can be easily exchanged after measurement by lateral flow of fluid through the flow cell. This ability permits rapid and simple testing for serial measurements. Also, the flow cell configuration is compatible with lithographic processing on the confining surfaces. The flat surfaces of the flow cell are easier to pattern than the permanently curved surface of, for example, a convex lens.

The use of the flow cell in conjunction with a movable lens provides a simple procedure for moving the point of contact between top and bottom confining surfaces. As noted above, the geometry of the confining surface can be readily controlled and easily varied by moving the contact point of the lens with the flow cell. Contacting the flow cell in two different points results in two different surfaces. Due to the scale of the flow cell relative to the field of view in the imaging device, movements result in small well-defined changes. The geometry of the confining surface can be measured in situ or calculated prior to testing using conventional interferometry measurements or measurements of the fluorescence intensity profile of a homogeneous solution of a small fluorescent molecule.

The use of a flow cell to contain the sample fluid instead of a convex surface such as a lens opens up a wider and more versatile list of materials to use for the confining surfaces. Lenses are made up of a limited number of materials, but cover slips are made of a wide variety of materials, such as mica, plastics and sapphire, that are not commonly used for lenses. The wide range of material compositions for the confining surfaces in a FC-CLIC system provides greater flexibility and versatility in the testing environment. In addition, the materials used to prepare the flow cell are inexpensive. A sample chamber can be composed entirely of disposable parts, eliminating the need for meticulous cleaning between experiments.

In the operation of the CLIC or FC-CLIC device, a sample to be measured is applied to the sample measurement surface, before or after the convex lens is moved into contact with the surface. The lens may be lowered to the surface before or after the sample is applied. In some embodiments, the lens is moved into contact with the surface before the sample liquid is applied and the sample is drawn into the gap defined by the test surface and the lens by wicking or capillary action. In other embodiments, the lens is raised, the sample liquid is applied and the lens is gently lowered onto the cover slip. As noted above, the lens-coverslip distance ("gap") varies smoothly from zero at the point of contact, to hundreds of microns at radii far from the point of contact. The molecules can only occupy space where the gap is equal to or greater than their diameter, that is, the molecule is excluded from those areas under the lens where the gap is less than the molecular size. Measurement of the distance of the onset of fluorescence from the center point, coupled with information regarding the curvature of the lens surface provides a measurement of the molecular size.

The CLIC and FC-CLIC systems can also be used to characterize the molecular size distributions of mixtures of molecules of a few sizes by analyzing the first- and second-derivatives of the total fluorescence intensity with respect to radius from the point of contact. These profiles can exhibit a 'kink', or distinguishable feature, at the radius of exclusion corresponding to each constituent molecule in the mixture. In addition, by employing particle tracking software, one may determine the distribution of diffusion coefficients of molecules as a function of gap height as a diagnostic of molecular mixtures. For example, in characterizing a mixture of large and small molecules, one would detect a higher fraction of molecules with low diffusion coefficients further from the contact point than in the case of a homogeneous sample of small molecules.

In some embodiments, the analyte is fluorescent or fluorescently labeled. The molecules can be inherently fluorescent, or they can be modified with a fluorescent tag. By way of example, the analyte can be covalently labeled with a fluorescent dye such as Alexa Fluor dyes. For protein analytes, the protein can be fused with a green fluorescent protein marker (*Nat Methods* 2 (12): 905-9). In most instances, the size of the label is not expected to interfere with the measurement. In other embodiments, a protein-specific fluorescent antibody can be used. In this instance, the molecular size of a particular protein could be determined without the need to purify the sample. In other embodiments, the samples can be inherently fluorescent, as for example proteins are under short wave ultraviolet irradiation. In such instances, additional measures can be taken such as using 'fluorescent-free' materials in the construction of the device to prevent high background fluorescence.

The CLIC and FC-CLIC systems can be used to measure the distribution or sizes of molecules of about 10 nm to about 1000 nm, such as DNA ranging from ~2,000-48,000 bp, 200 nm lipid vesicles, and polystyrene spheres with diameters ranging from 20-200 nm. The method can also be used with smaller particles, such as individual protein molecules, fluorescent micelles, and short DNA oligonucleotides. The CLIC and FC-CLIC systems can operate over a range of analyte concentrations, e.g. 10 pM-10 µM Low liquid volumes also may be employed (1-100 µL).

While measurements of molecular size are likely to have the greatest impact as a medical diagnostic, the CLIC and FC-CLIC system also enable several new types of single-molecule measurements that may interest researchers. These measurements include a) fluorescence measurements on single immobilized molecules in the presence of a high background concentration of freely diffusing fluorescent molecules; and b) long-time observation of single freely diffusing fluorescent molecules. In both cases, the thin confinement provided by the CLIC and FC-CLIC systems create the optical conditions for higher quality single-molecule imaging than was previously possible.

Figure 4:
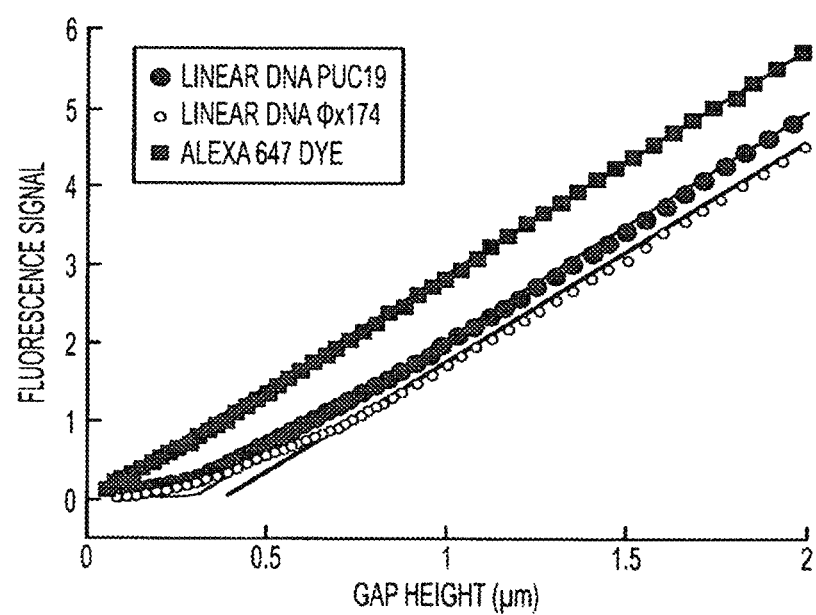
FIG. 4 illustrates normalized fluorescence profiles of solutions (Concentration=1.4 nM) of two lengths of linear DNA, pUC19 (2.7 kbp) (large dot) and φX174 (5.4 kbp) (small dot), and free Alexa 647 dye (Concentration=50 nM). Linear fits to these profiles are performed at large gap heights (0.6 µm<h<2.7 µm). The fluorescence profiles have been normalized to have equal slopes in this region.

The CLIC system has been used to characterize the size of a range of fluorescently labeled molecules. FIG. 4 delineates the fluorescence signal, measured as a function of gap height, for ensembles of linear DNA molecules, and free dye (Alexa 647). To a first approximation, the molecules can be treated as hard spheres, valid for $h \gg d_{hs}$. The molecular diameter, $d_{hs}$, can be determined from the x-intercept of the linear fit to the fluorescence profile in this region. For linear DNA samples of φX174 and pUC 19, $r_{hs}=0.19\pm0.02$ µm and $0.15\pm0.03$ µm respectively. These estimates were in good agreement with literature-inferred radii of gyration, $r_{gyr}=0.20$ µm and 0.13 µm respectively.

For sufficiently large molecules and negligible surface interactions, $r_{hs}$ provides an accurate measure of molecular size. In situations where surface interactions dominate, such as when the salt concentration is sufficiently low that the Debye length is non-negligible, molecules can be repelled from or attracted to the surface, altering the observed $R_{excl}$, the radius of exclusion for the molecules of interest. Such contributions to $R_{excl}$ due to electrostatic interactions can be calibrated a priori and taken into account in calculating $r_{hs}$. Alternatively, by coating the surface with a neutral monolayer such as polyethylene glycol (PEG), attractive interactions may be suppressed.

In one embodiment, the device and method can be used to measure the distribution of sizes and shapes of amyloid fibrils. The aggregation of amyloids and their structural traits are associated with the development of neurodegenerative diseases. Since this device and method can be used to characterize the change in size and shape of samples of amyloid fibrils as the diseases progress, it can serve as an important medical diagnostic tool.

A standard working criteria for single-molecule detection is for the detection volume to be occupied by less than one fluorophore on average. Therefore, decreasing the detection volume enables single-molecule detection at higher background fluorophore concentration. Near the lens contact point, the detection volume is smaller in depth than that of either confocal or TIRF imaging and is of comparable extent within the imaging plane. Single immobilized molecules can therefore be detected against a higher background concentration of fluorophores by CLIC or FC-CLIC than by TIRF or confocal microscopy. Details and comparison of CLIC, FC-CLIC and conventional imaging systems is found in Table 1. The improved rejection of background was demonstrated by comparing images taken with CLIC to images taken with TIRF. Singly labeled DNA oligonucleotides were used as a model system. The sample was immobilized on a coverslip and imaged in the presence of a variable concentration of free dye.

Through-the-objective TIRF illuminates a thin sheet of solution adjacent to the coverslip-solution interface. The detection volume is approximately $V_{det} = \pi \mathit{r}d^2 h^{TIRF}$, where $\mathit{r}d \sim \lambda/2\,NA$ is the radius of a diffraction-limited spot, and $h^{TIRF} \sim \lambda/2\pi$ is the evanescent decay length. □ In a typical setup with illumination at $\lambda=633$ nm and an objective with numerical aperture NA=1.45, $\mathit{r}d = 218$ nm and $h^{TIRF}=101$ nm. Single-molecule detection via TIRF is possible only when the fluorescent background concentration $C_{max}^{TIRF} < 180$ nM. The single-molecule concentration limit for CLIC is $$C_{max}^{CLIC} = \frac{h^{TIRF}}{h^{CLIC}} C_{max}^{TIRF}.$$

Figure 5:
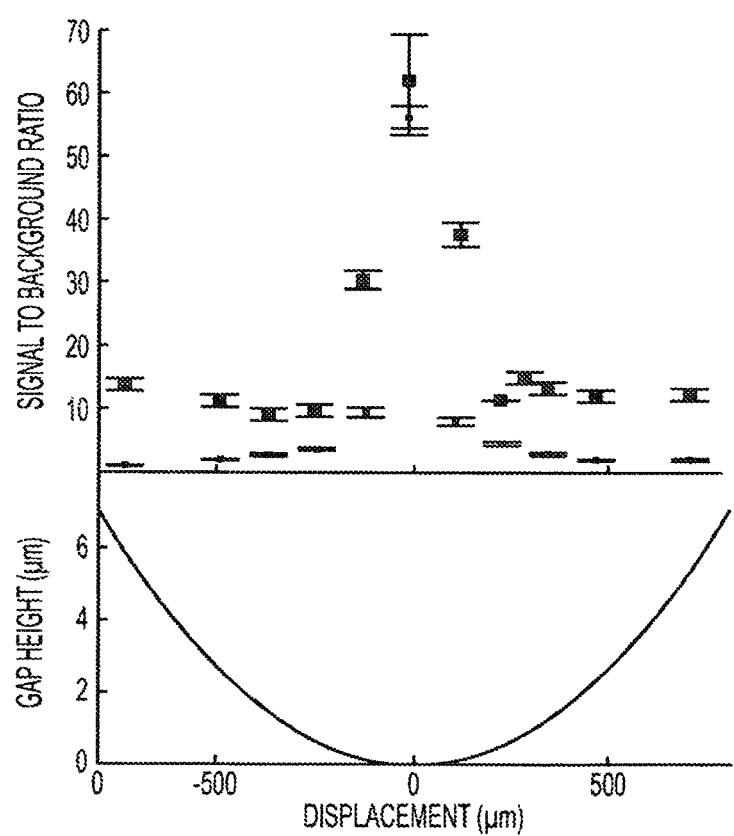
FIG. 5 shows the signal-to-background ratio as a function of confinement (displacement form contact point), for CLIC imaging of surface-immobilized fluorescent polystyrene beads immersed in 50 nM Alexa 647 dye.
Figure 6:
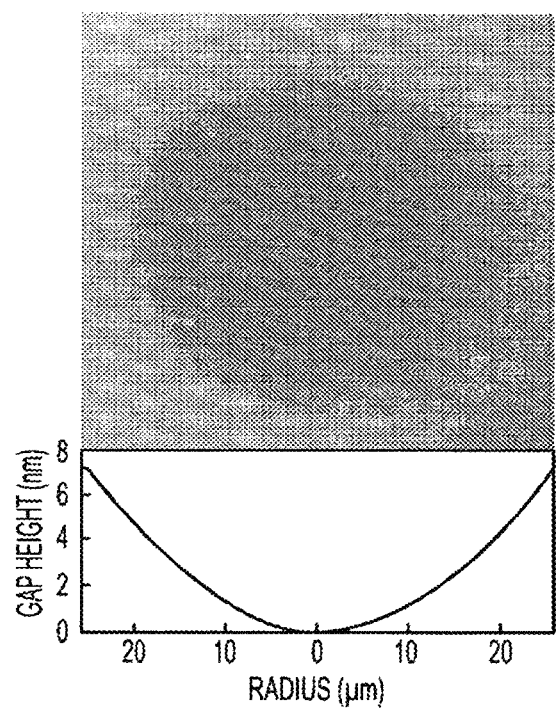
FIG. 6 shows a CLIC image of surface-tethered DNA oligonucleotides in the presence of 0.2 µM Alexa 647 dye, imaged with a power of 6 mW and exposure time of 0.1 s. A nonlinear contrast scale is applied to permit visualization in the same image of the single molecules at small radius from the point of contact and the background fluorescence at large radius from the point of contact.
Figure 7:
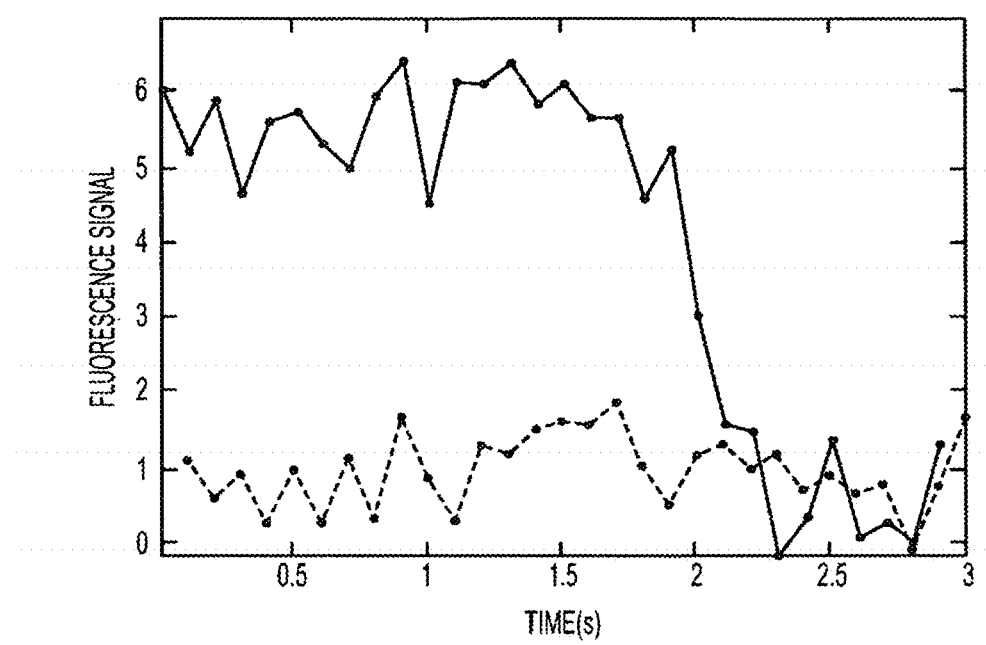
FIG. 7 shows a photobleaching timetrace of a single DNA molecule (circled in FIG. 6).
Figure 8:
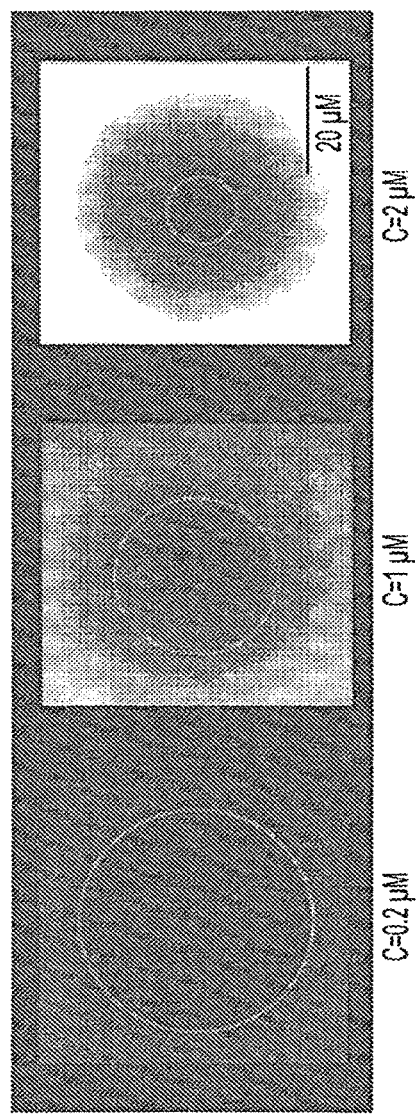
FIG. 8 shows CLIC images of free dye (Alexa 647) and surface-tethered DNA oligonucleotides at dye concentrations of 0.2 µM, 1 µM, and C=2 µM, with equal-fluorescence contours indicated. A linear contrast is used.

The improved rejection of background under CLIC imaging is shown in FIG. 5. Single immobilized fluorophores were imaged against a background of up to 4 μM of free dye, 20-fold higher than $C_{max}^{TIRF}$. FIG. 5 shows the signal-to-background ratio as a function of confinement, for CLIC imaging of surface-immobilized fluorescent polystyrene beads immersed in 50 nM Alexa 647. Probe illumination corresponds to $\lambda=633$ nm, and P=120 μW. Under TIRF illumination conditions the background becomes independent of $h^{CLIC}$ when $h^{CLIC} > h^{TIRF}$. FIG. 6 shows a CLIC image of surface-tethered DNA oligonucleotides in the presence of 0.2 μM Alexa 647 at P=6 mW. A nonlinear contrast scale was applied to permit visualization in the same image of the single molecules at small r and the background fluorescence at large r. FIG. 7 shows a photobleaching timetrace of a single molecule (circled in FIG. 6), and a timetrace of the fluorescence from a point where there was no immobilized molecule. FIG. 8 are CLIC images of free dye (Alexa 647) at concentrations of 0.2 μM, 1 μM, and C=2 μM, with equal-fluorescence contours indicated. At 2 μM Alexa 647, single oligos molecules may be detected within a disk of radius r=21 μm, corresponding to $h^{CLIC}=5$ nm, in good agreement with the expected detection limit.

Comparison of the imaging characteristics of the CLIC method as compared to conventional methods is shown in the table.

TABLE 1

| Imaging modality | Dimensions of imaging volume L × W × H (μm) | Max concentration of single molecules | Observation time (D = 100 μm²/s) | # of molecules observed simultaneously |
|---|---|---|---|---|
| TIRF | 100 × 100 × 0.1 | 180 nM | 500 μs (vertical) | hundreds |
| Confocal | π × 0.3² × 1 | 50 nM | 200 μs (in-plane) | 1 |
| Zero-mode waveguides | .04 × .04 × .02 | 50 μM | 2 μs (vertical) | Thousands; 1 per waveguide |
| ABEL trap | 3 × 3 × 0.8 | 200 pM | 2 s (photobleaching) | 1 |
| Convex Lens-Induced Confinement (CLIC) | 100 × 100 × 0.005 | 4 μM | 25 s (in-plane) | hundreds |

The foregoing illustrates one specific embodiment of this invention. Other modifications and variations of the invention will be readily apparent to those of skill in the art in view of the teaching presented herein. The foregoing is intended as an illustration, but not a limitation, upon the practice of the invention. It is the following claims, including all equivalents, which define the scope of the invention.

The invention claimed is:

1. A method for imaging a molecule, comprising:
providing a flow cell already having molecule(s) and/or adapted for receiving a fluidic sample comprising molecule(s) to be analyzed, said flow cell comprising:
an upper sheet and a lower sheet spaced apart from one another by side walls, wherein the upper sheet, the lower sheet and the side walls define an enclosure adapted for being filled with a fluid,
wherein at least one of the bottom sheet and upper sheet is transparent, and
wherein the upper sheet is deflectable for providing an inner convex surface positioned tangent to an inner planar surface of the lower sheet, the inner convex surface of the upper sheet and the planar inner surface of the lower sheet forming a nanoscale deflectable plano-concave gap confining molecules to be imaged;
deflecting said upper sheet by applying thereon a controlled outside force, said deflecting creating said convex surface and forming said nanoscale deflectable plano-concave gap at a centered point of contact of said force;
filling entirely the enclosure of the flow cell with a fluid, wherein said filling is carried out before or after said deflecting, and
wherein said fluid comprises at least one sample molecule if the sample molecule is not already present at the inner surface of the lower sheet or at the inner convex surface of the upper sheet; and
imaging molecules at an imaging zone including said centered point of contact while maintaining said controlled outside force.

2. The method of claim 1, wherein said deflecting comprises gradually applying a pressure against an outer surface of the upper sheet.

3. The method of claim 1, wherein the flow cell comprises a pair of apertures for filling said enclosure with said fluid and for allowing a flow of fluid through the flow cell, wherein the upper sheet, lower sheet and the side walls provide altogether a sealed flow cell having only two apertures to access the enclosure.

4. The method of claim 1, wherein said molecule(s) are immobilized on at least one of the inner surface of the upper sheet and inner surface of the lower sheet.

5. The method of claim 1, wherein at least one of the inner surface of the upper sheet and inner surface of the lower sheet is chemically functionalized.

6. The method of claim 1, wherein at least one of the inner surface of the upper sheet and inner surface of the lower sheet comprises at least one of patterns, posts and dimples.

7. The method of claim 1, further comprising analyzing said imaging with at least one of an imaging software and a particle tracking software.

8. The method of claim 7, wherein said software analyzes an image of light emission from molecule(s) at said imaging zone to assess one or more of: molecular size, diameter of the molecule(s), distribution of diameters of a plurality of molecules, shape of a molecule(s), and aspect ratio of the molecule(s), length of molecule(s), and diffusion of molecule(s).

9. A system for imaging a molecule, comprising:
a flow cell already having molecule(s) and/or adapted for receiving a fluidic sample comprising molecule(s) to be analyzed, said flow cell comprising an enclosure having a planar lower sheet and a deflectable upper sheet forming a nanoscale plano-concave gap confining molecules to be imaged at an imaging zone including a centered point of contact when said upper sheet is deflected by applying thereon a controlled outside force;
a planar surface for positioning the flow cell,
a deflector to apply a controlled outside force at an external surface of the enclosure, said controlled outside force deflecting the enclosure to form said nanoscale plano-concave gap;
a light source for illuminating the nanoscale plano-concave gap of the flow cell; and
an imaging device for detecting light passing through said plano-concave gap at said imaging zone including a centered point of contact.

10. The system of claim 9, wherein the deflector comprises a convex surface that can be raised and lowered into contact with the flow cell.

11. The system of claim 9, wherein at least one of the planar surface and the deflector comprises positioning capability in x-, y- and z-directions.

12. The system of claim 9, wherein the light source is a laser, a lamp or a light emitting diode (LED).

13. The system of claim 9, further comprising at least one of a computer and software for imaging analysis.

14. A flow cell for imaging a molecule, comprising:
an enclosure adapted for being filled with a fluid, the enclosure comprising a pair of apertures, an upper sheet and a lower sheet spaced apart from one another by side walls,
wherein the upper sheet, lower sheet and the side walls provide altogether a sealed enclosure having only two apertures,
wherein at least one of the bottom sheet and the upper sheet is transparent, and
wherein the upper sheet is deflectable when applying thereon a controlled outside force, said deflecting creating an inner convex surface positioned tangent to an inner planar surface of the lower sheet, the inner convex surface of the upper sheet and the planar inner surface of the lower sheet forming a nanoscale deflectable plano-concave gap confining molecules to be imaged at an imaging zone including a centered point of contact of said force.

* * * * *